(12) United States Patent
Liu et al.

(10) Patent No.: US 12,128,742 B2
(45) Date of Patent: Oct. 29, 2024

(54) AIR PURIFIER

(71) Applicant: Hangzhou Newaon Electronic Technology Co., Ltd., Zhejiang (CN)

(72) Inventors: Jiangyun Liu, Zhejiang (CN); Mingwei Ding, Zhejiang (CN)

(73) Assignee: Hangzhou Newaon Electronic Technology Co., Ltd., Hangzhou (CN)

( * ) Notice: Subject to any disclaimer, the term of this patent is extended or adjusted under 35 U.S.C. 154(b) by 732 days.

(21) Appl. No.: 17/335,066

(22) Filed: May 31, 2021

(65) Prior Publication Data
US 2022/0297511 A1 Sep. 22, 2022

(30) Foreign Application Priority Data

Mar. 16, 2021 (CN) .......................... 202110282031.0

(51) Int. Cl.
| | |
|---|---|
| *B01D 53/22* | (2006.01) |
| *B01D 53/02* | (2006.01) |
| *B03C 3/00* | (2006.01) |
| *B60H 3/00* | (2006.01) |
| *B60H 3/06* | (2006.01) |
| *F24F 8/108* | (2021.01) |
| *F24F 8/158* | (2021.01) |

(Continued)

(52) U.S. Cl.
CPC ......... *B60H 3/0071* (2013.01); *B60H 3/0608* (2013.01); *F24F 8/108* (2021.01); *F24F 8/158* (2021.01); *F24F 8/22* (2021.01); *B60H 2003/0675* (2013.01); *B60H 2003/0691* (2013.01); *F24F 8/30* (2021.01)

(58) Field of Classification Search
CPC ............................. A61L 9/205; B01D 53/885
USPC ................... 422/22, 24, 121; 96/4, 15, 108
See application file for complete search history.

(56) References Cited

U.S. PATENT DOCUMENTS

| | | | |
|---|---|---|---|
| 2015/0064061 A1* | 3/2015 | Taghipour | .............. B64D 13/06 422/4 |
| 2017/0326264 A1 | 11/2017 | Kim et al. | |

(Continued)

FOREIGN PATENT DOCUMENTS

| | | |
|---|---|---|
| CN | 107631369 A | 1/2018 |
| CN | 107702217 A | 2/2018 |

(Continued)

OTHER PUBLICATIONS

European Search Report of European Patent Application No. 21176564.9 issued on Nov. 22, 2021.

*Primary Examiner* — Monzer R Chorbaji

(57) ABSTRACT

The present invention relates to an air purifier comprising a housing with an air inlet and an air outlet. A filter module, a power supply module, a drive module and a processing module are sequentially arranged in the housing along an airflow direction. The drive module gives a drive force to the air, so that the air enters into the housing from the air inlet, then in turn flows through the filter module, the power supply module, the drive and processing modules. The filter module filters out large particle pollutants in the air such as dust. The power supply module is used to supply power to the drive module and the processing module. The processing module is used to remove bacteria and organic pollutants in the air. Therefore, the degree of air purification can be improved, so that the air is purified to the ideal state as much as possible.

15 Claims, 11 Drawing Sheets

(51) Int. Cl.
*F24F 8/22* (2021.01)
*F24F 8/30* (2021.01)

(56) References Cited

U.S. PATENT DOCUMENTS

2017/0348455 A1* 12/2017 Kim ...................... B01D 53/86
2021/0046411 A1   2/2021 Lofvendahl

FOREIGN PATENT DOCUMENTS

| CN | 208253779 U | 12/2018 | |
|---|---|---|---|
| CN | 219243818 U | 6/2023 | |
| WO | WO-2005039659 A1 * | 5/2005 | ............... A61L 9/16 |
| WO | 2020116729 A1 | 6/2020 | |

\* cited by examiner

AIR PURIFIER

CROSS-REFERENCE TO RELATED APPLICATION

The present application claims the priority of China application No. 20211 0282031.0, filed on Mar. 16, 2021. The entirety of the above-mentioned patent application is incorporated by reference herein and made a part of this specification.

BACKGROUND

Technical Field

The present invention relates to a field of in-vehicle equipment, in particular to an air purifier.

Description of Related Art

The vehicle exhaust content and the dust content around a vehicle during the driving seriously exceed the standard, which seriously affects the health of the people in the car. For this reason, the people began to use vehicle-mounted purifiers. However, the current vehicle-mounted purifiers can only perform simple dust removal, and the ideal purification effect cannot be achieved.

SUMMARY

In order to improve the air purification effect of an air purifier and achieve the ideal purification effect as much as possible, an air purifier provided by the present invention adopts the following technical solutions.

An air purifier comprises a housing provided with an air inlet and an air outlet; a filter module, a drive module and a processing module are sequentially arranged in the housing along an airflow direction; the drive module is used to drive the air to flow from the air inlet to the air outlet; the processing module in turn comprises a Titanium dioxide plate and an LED light plate sequentially installed in the housing along the airflow direction; and the LED light plate irradiates a Titanium dioxide plate, the LED light plate irradiating UVA and UVC.

By adopting the above technical solution, the drive module gives a drive force to the air, so that the air enters into the housing from the air inlet, then in turn flows through the filter module, the drive module and the processing module. The filter module filters out large particle pollutants in the air such as dust. The UVA and UVC irradiated by the LED light plate destroy and change the DNA structure of microorganisms, so that the bacteria immediately die or cannot reproduce their offspring to achieve the purpose of sterilization. The titanium dioxide plate will produce a photocatalytic reaction similar to photosynthesis under the irradiation of light, resulting in strong oxidative carboxyl free radicals and anionic free radicals, which can effectively decompose various organic compounds, destroy the cell membrane of bacteria and virus proteins, and remove organic pollutants. Therefore, the degree of air purification can be improved, so that the air is purified to the ideal state as much as possible.

Preferably, the housing is provided upright; the housing comprises an inner housing and an outer housing sleeved outside the inner housing; a plurality of the air inlets are provided on the outer wall of the outer housing along the circumferential direction of the outer housing; the air outlet is provided on an upper end of the outer housing and communicated with an inner cavity of the inner housing; a lower end of the inner housing is provided with an air guide port communicated with the inner cavity of the inner housing; the outer wall of the inner housing is provided with convex edges along its length direction; the convex edges, the outer wall of the inner housing and the inner wall of the outer housing form a diversion cavity communicated with the air inlet and the air guide port; and the filter module, the drive module and the processing module are located between the air guide port and the air outlet.

Preferably, a plurality of air guide ribs are provided outside the outer housing along the axial direction of the outer housing and spaced apart along the circumferential direction of the outer housing; and the air inlets are located between the air guide ribs.

Preferably, the processing module further comprises a top cover installed with a circuit board; the LED light plate is connected with the circuit board; the upper end of the outer housing is provided in a form of an opening; and the top cover is installed at the upper end opening of the outer housing and is removably connected with the outer housing.

Preferably, an upper end of the inner housing is fixedly mounted along the axial direction thereof with at least two first mounting posts; an upper end of the first mounting post is fixedly mounted with a first mounting protrusion; the LED light plate is provided with first insertion grooves; and the LED light plate is abutted against the first mounting post and the first mounting protrusions are inserted into the first insertion groove.

Preferably, an upper end of the inner housing is fixedly mounted along the axial direction thereof with at least two second mounting posts; an upper end of the second mounting post is fixedly mounted with a second mounting protrusion; the top cover is provided with a second insertion grooves; and the top cover is abutted against the second mounting post and the second mounting protrusions are inserted into the second insertion grooves.

Preferably, the inner housing comprises an upper housing and a lower housing located below the upper housing; the lower housing is removably connected with the outer housing; the filter module is installed within the lower housing; and the drive module is installed within the upper housing.

Preferably, a lower end of the outer housing is provided in a form of an opening, and the lower end opening of the outer housing is used to remove the lower housing.

Preferably, a lower end of the lower housing is fixedly provided with a base for closing the lower end of the lower housing and the lower end of the outer housing; and a plurality of the air guide ports are provided on the side wall of the lower housing along the circumferential direction of the outer wall of the lower housing.

Preferably, an upper end of the base is recessed downwards to form a plurality of overflow recesses provided along the radial direction of the base and along the circumferential direction of the lower housing, and one overflow recess corresponds to one air guide port.

Preferably, the filter module comprises an activated carbon filter and a HEPA filter that are sequentially disposed along the airflow direction.

Preferably, the drive module is removably connected with the inner housing.

Preferably, the power supply module is provided between the filter module and the drive module and is installed within the inner housing, and the air from the air inlet to the air outlet flows through the power supply module.

Preferably, the power supply module comprises a series of battery units that are disposed along the circumferential direction of the inner housing and a mounting seat that comprises a mounting sleeve sleeved outside the battery unit, one mounting sleeve corresponds to one battery unit, and the mounting sleeve is fixedly connected with the inner wall of the inner housing.

Preferably, the mounting seat further comprises a connector for fixedly connecting adjacent mounting sleeves; the mounting sleeve is circular in section; the mounting sleeve and the connector enclose a passageway through which the air flows through the drive module.

Preferably, a negative ion generator module is provided between the drive module and the filter module.

DESCRIPTION OF REFERENCE SIGNS

1—air inlet; 2—air outlet; 3—filter module; 4—power supply module; 5—drive module; 6—processing module; 7—inner housing; 8—outer housing; 9—air guide rib; 10—sealing convex ring; 11—convex edge; 12—base; 13—diversion cavity; 14—air guide port; 15—first close unit; 16—second close unit; 17—overflow recess; 18—upper housing; 19—lower housing; 20—annular supporter; 21—activated carbon filter; 22—HEPA filter; 23—mounting seat; 24—mounting sleeve; 25—connector; 26—battery unit; 27—passageway; 28—Titanium dioxide plate; 29—LED light plate; 30—circuit board; 31—top cover; 32—connection seat; 33—first connecting slot; 34—second connecting slot; 35—first mounting post; 36—first mounting protrusion; 37—first insertion groove; 38—mounting bump; 39—second mounting post; 40—second mounting protrusion; 41—second insertion groove; 42—negative ion generator module.

DESCRIPTION OF THE EMBODIMENTS

The following describes the present invention in further detail with reference to FIGS. 1-13.

Figure 1:
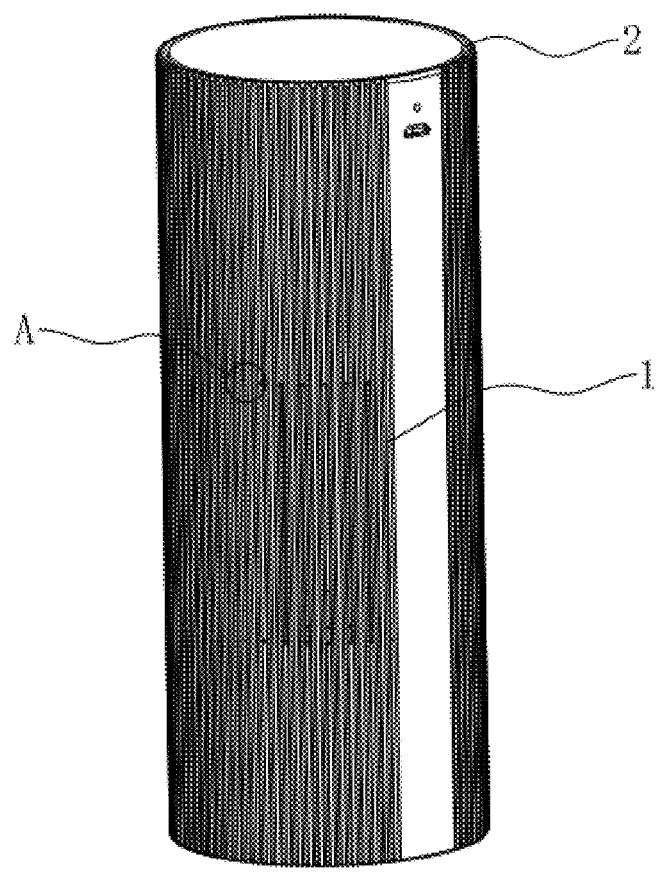
FIG. 1 is a schematic structural view of an embodiment.
Figure 2:
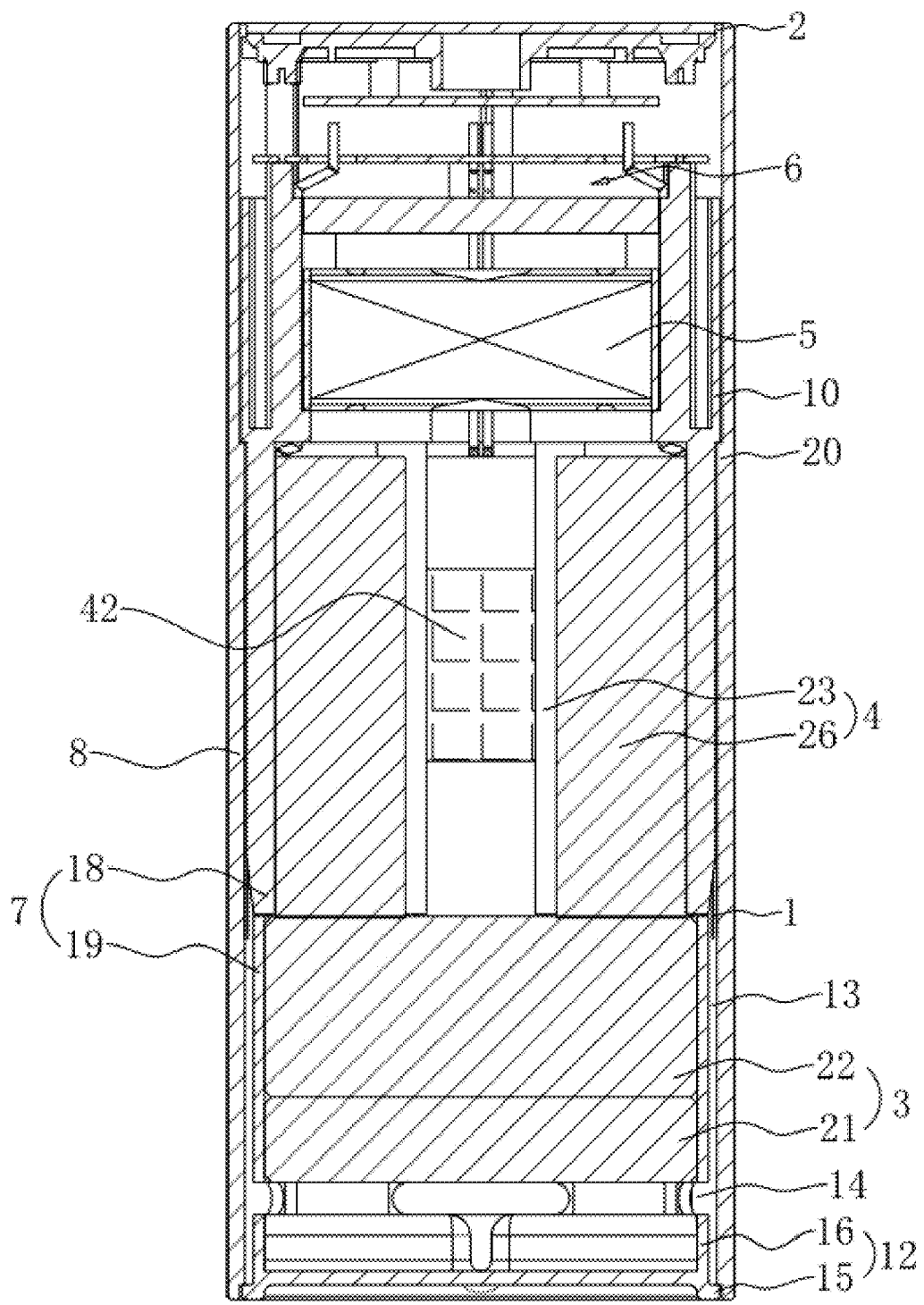
FIG. 2 is a cross-sectional view of the embodiment.

The embodiments of the present invention disclose an air purifier. Referring to FIGS. 1 and 2, an air purifier comprises a housing provided with an air inlet 1 and an air outlet 2. A filter module 3, a power supply module 4, a drive module 5 and a processing module 6 are sequentially arranged in the housing along an airflow direction.

The drive module 5 gives a drive force to the air, so that the air enters into the housing from the air inlet 1, then in turn flows through the filter module 3, the power supply module 4, the drive module 5 and the processing module 6. The filter module 3 filters out large particle pollutants in the air such as dust. The power supply module 4 is used to supply power to the drive module 5 and a processing module 6. The processing module 6 is used to remove bacteria and organic pollutants in the air. Therefore, the degree of air purification can be improved, so that the air is purified to the ideal state as much as possible.

Referring to FIG. 2, in order to more evenly purify and treat the air in the vehicle, the housing comprises an inner housing 7 and an outer housing 8 sleeved outside the inner housing 7. The inner housing 7 and the outer housing 8 each is a hollow cylinder. And, when the air purifier is in a used state, the inner housing 7 and the outer housing 8 each are placed in a vertical direction. The processing module 6 is installed at an upper end of the outer housing 8 and closes the upper end of the outer housing 8. The filter module 3, the power supply module 4, the drive module 5 are sequentially installed within the inner housing 7 from down to top. Meanwhile, a lower end of the outer housing 8 is fixedly provided with a base 12 for closing the lower end of the inner housing 7 and a lower end of the outer housing 8.

Figure 3:
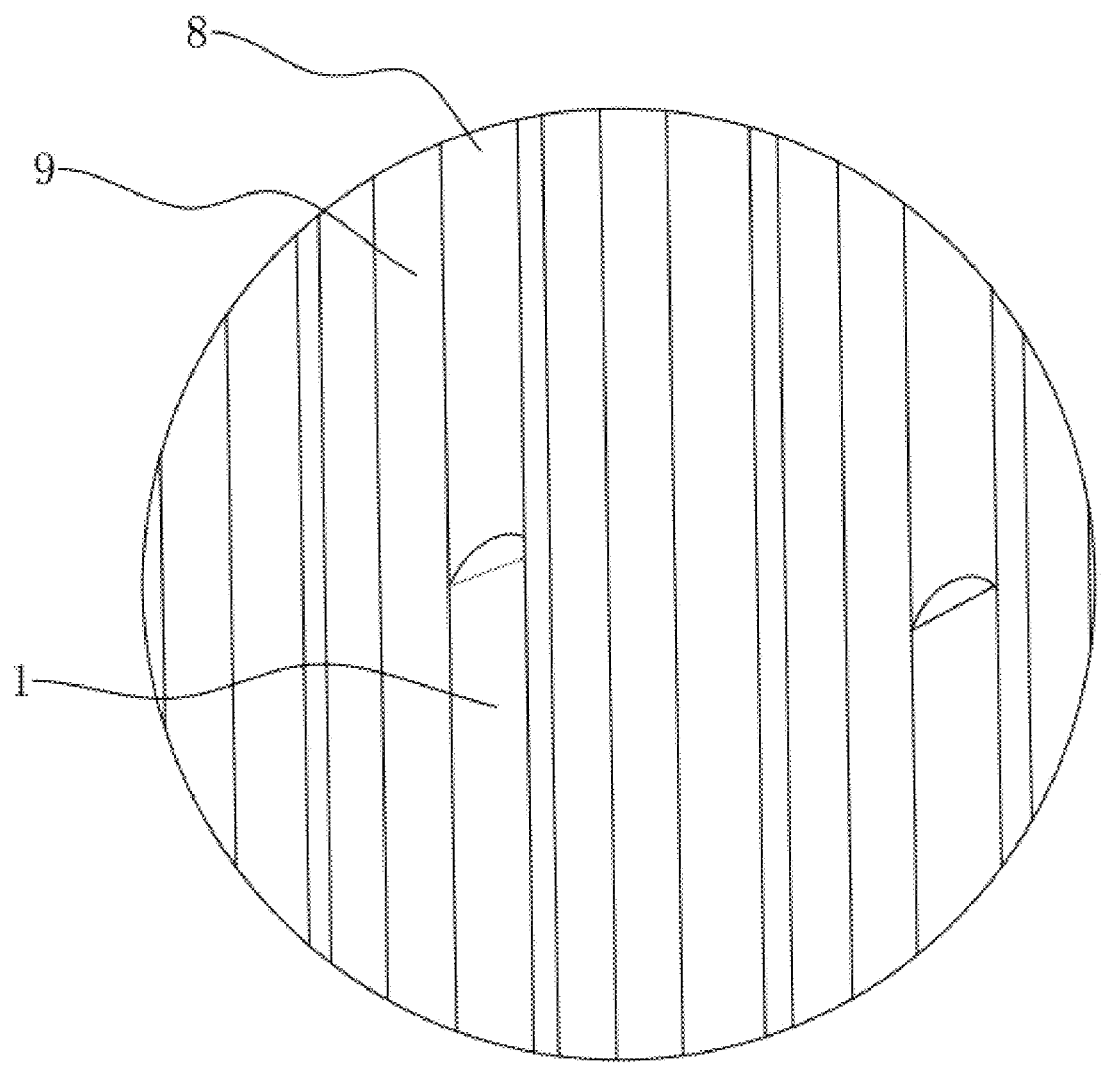
FIG. 3 is an enlarged view of part A in FIG. 1.

Specifically, referring to FIGS. 1 and 3, a plurality of air guide ribs 9 are provided outside the outer housing 8 along the axial direction of the outer housing 8 and spaced apart along the circumferential direction of the outer housing 8. The plurality of the air inlets 1 are provided on the outer wall of the outer housing 8 along the circumferential direction of the outer housing 8. Each of the air inlets 1 is located between the two adjacent air guide ribs 9. Referring to FIG. 2, the air inlet 1 is communicated with an inner cavity of the outer housing 8. The upper end opening of the outer housing 8 forms the air outlet 2.

Figure 4:
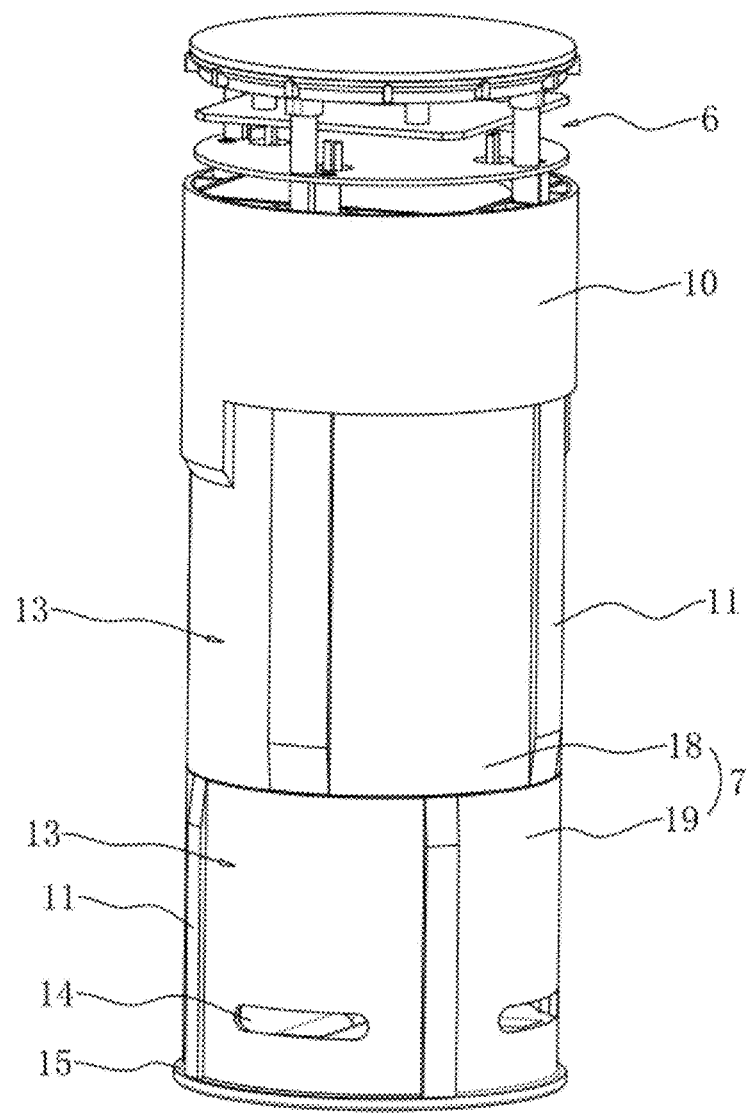
FIG. 4 is a schematic structural view of the embodiment with an outer housing removed.

Referring to FIGS. 2 and 4, the outer wall of the inner housing 7 is fixedly provided with a sealing convex ring 10 along the circumferential direction thereof. The outer wall of the inner housing 7 is provided along the axial direction thereof with convex edges 11 extending from the lower end face of the sealing convex ring 10 to the lower end face of the inner housing 7. There are four convex edges 11 spaced apart evenly along the circumferential direction of the inner housing 7. When the inner housing 7 is inserted in the outer housing 8, both the sealing convex ring 10 and convex edges 11 abut against the inner wall of the outer housing 8 and form an interference fit with the outer housing 8. The sealing convex ring; 10, adjacent two convex edges 11, the inner wall of the outer housing 8, the outer wall of the inner housing 7 and the base 12 enclose a closed diversion cavity13. The side wall of the inner housing 7 is provided with an air guide port 14 communicated with the inner cavity of the inner housing 7. The air guide port 14 is located at the lower end of the inner housing 7. There are a plurality of air guide ports 14 along the circumferential direction of the inner housing 7, and one air guide port 14 corresponds to one diversion cavity 13. The diversion cavity 13 communicates the air guide ports 14 with the air inlets 1.

Figure 5:
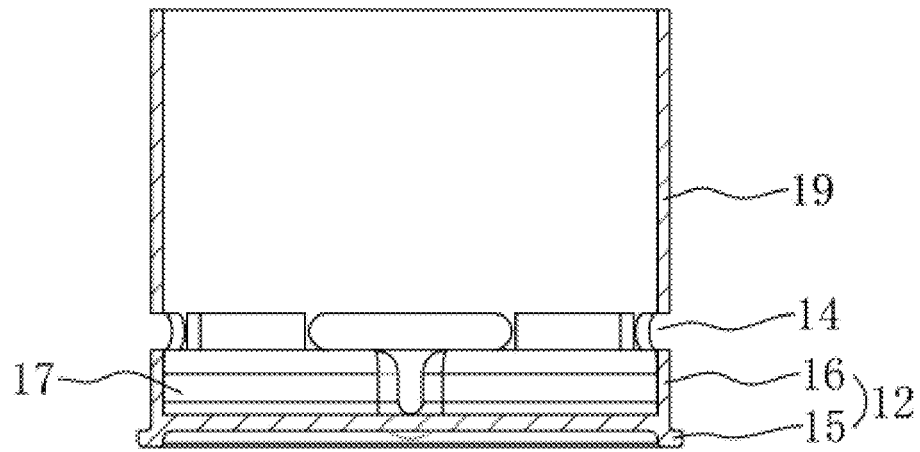
FIG. 5 is a cross-sectional view of a lower housing and a base in the embodiment.
Figure 6:
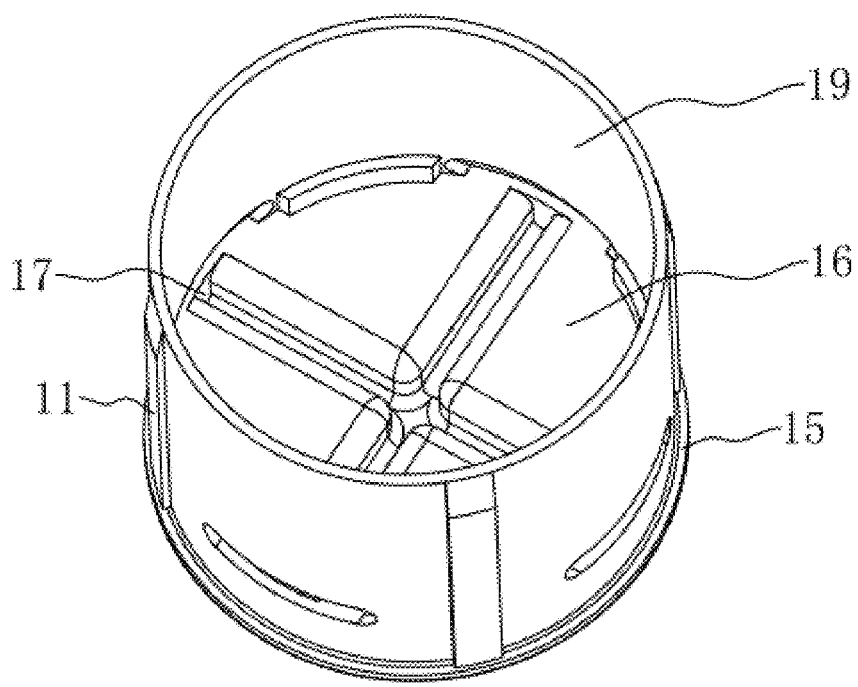
FIG. 6 is a schematic structural view of the lower housing and the base in the embodiment.

Referring to FIG. 2, the base 12 includes a first closing unit 15 inserted in the lower end of the outer housing 8 and a second closing unit 16 fixedly connected to the lower end of the inner housing 7. Referring to FIGS. 5 and 6, the second closing unit 16 is a hollow cylinder with a sealed upper end. The first closed unit 15 is a circular ring and is fixedly sleeved outside the second closed unit 16. The lower end faces of the first closed unit 15 and the second closed unit 16 are located on the same plane. Referring to FIG. 2, when the first closing unit 15 is inserted in the outer housing 8 and the second closing unit 16 is fixedly connected to the lower end of the inner housing 7, the lower end of the outer housing 8 and the lower end of the inner housing 7 are both closed by the base 12.

When using this air purifier, the air enters the diversion cavity 13 from the air inlets 1 around the outer housing 8, enters the air guide ports 14 under the guidance of the diversion cavity 13, and flows through the air guide ports 14 into the inner cavity of the inner housing 7. After passing through the filter module 3, the power supply module 4, the drive module 5 and the processing module 6 in turn, the air enters the outer housing 8 from the upper end opening of the inner housing 7 and exits from the air outlet 2 on the outer housing 8, thus completing the purification. In this process, through the cooperation of the air inlets 1, the diversion cavity 13 and the air guide ports 14, the air purifier can collect the air around it instead of just a single point, so that the surrounding air can be collected and processed more evenly.

Referring to FIGS. 5 and 6, in order to allow the air purifier to be more stably placed on a placement plane when the air enters into the inner cavity of the inner housing 7 from the air guide ports 14, an upper end of the second closing unit 16 is recessed downward to form an overflow recess 17 provided along the radial direction of the second closing unit 16. There is a plurality of overflow recesses 17 along the circumferential direction of the second closing unit 16, and one overflow recess 17 corresponds to one air guide port 14. When the air enters the inner cavity of the inner housing 7 from the air guide ports 14, it will partly escape into the overflow recesses 17, so as to balance the upward force received by the air purifier due to the upward flow of a part of the air.

Referring to FIGS. 2 and 4, in order to replace the filter module 3 more conveniently, the inner housing 7 is divided into an upper housing 18 and a lower housing 19, both of which are a hollow cylinder. The power supply module 4 and the drive module 5 are installed within the upper housing 18, and the filter module 3 is installed within the lower housing 19.

Specifically, referring to FIGS. 2 and 4, The sealing convex ring 10 is provided on the outer periphery of the upper housing 18, and the inner wall of the outer housing 8 is provided with an annular supporter 20. When the upper housing 18 is inserted in the outer housing 8, the sealing convex ring 10 and the outer housing 8 are in an interference fit, and the sealing convex ring 10 abuts against the annular supporter 20, so that the upper housing 18 is fixedly connected to the outer housing 8. The outer periphery of the upper housing 18 and the lower housing 19 are both provided with convex edges 11. The convex edges 11 of the lower housing 19 is fixedly connected to the upper end surface of the first closing unit 15 so that the lower housing 19 is fixedly connected to the base 12. The air guide ports 14 are opened on the lower housing 19. Referring to FIG. 2, the filter module 3 includes an activated carbon filter 21 and a HEPA filter 22 that are fixedly installed within the lower housing 19 from bottom to top.

The air entering the inner cavity of the inner housing 7 from the air guide ports 14 passes through the activated carbon filter 21 and the HEPA filter 22 to filter out large particles of impurities such as dust to complete a first purification. Because the filter module 3 is installed in the lower housing 19 and the lower housing 19 is fixedly connected to the base 12, when the filter module 3 needs to be replaced, the base 12 can be directly pulled out of the outer housing 8, which is convenient for operation. During installation, it is only necessary to directly press the base 12 into the lower end of the outer housing 8. After the base 12 is installed in place, the lower housing 19 abuts against the upper housing 18.

Figure 7:
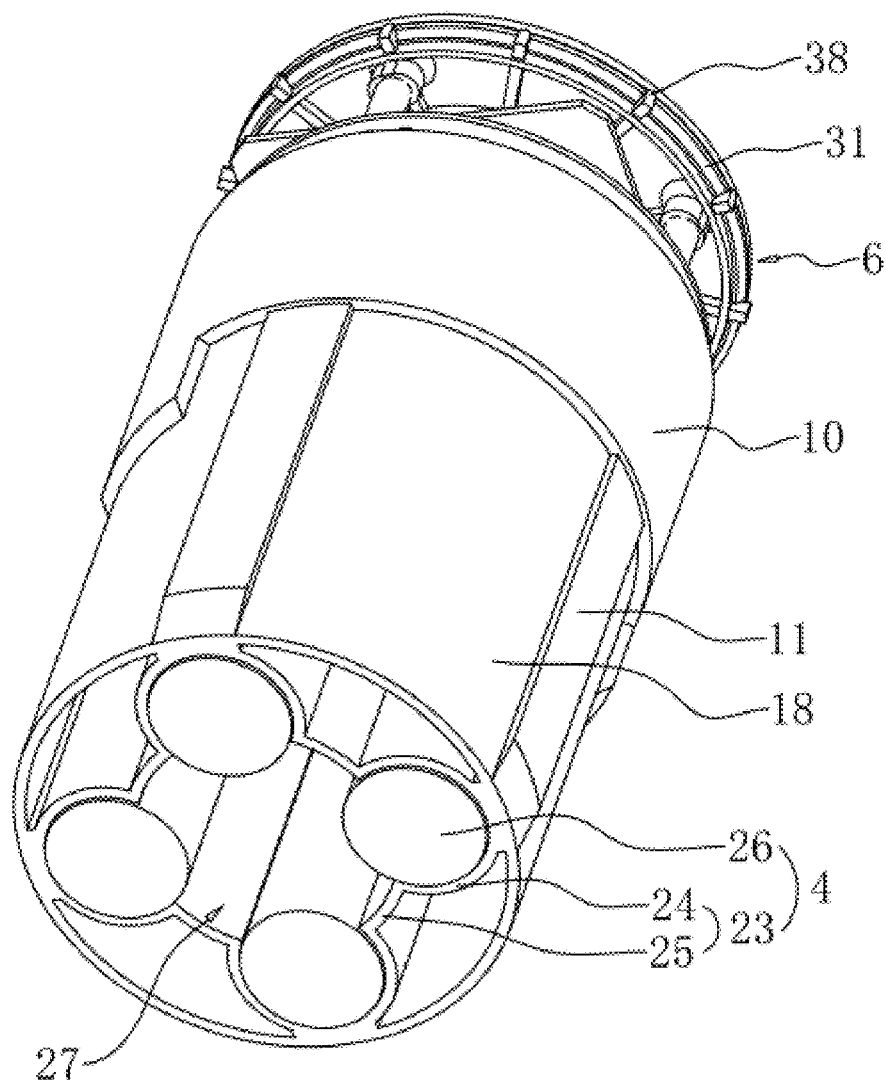
FIG. 7 is a schematic structural view of the embodiment with the outer housing and a filter module removed.

For better heat dissipation, referring to FIG. 7, the power supply module 4 includes four battery units 26 and a mounting seat 23. The mounting seat 23 includes a mounting sleeve 24 and a connector 25. The battery cells 26 are arranged in the circumferential direction of the upper housing 18. The mounting sleeve 24 is circular in section and is sleeved outside the battery units 26. One mounting sleeve 24 corresponds to one battery unit 26 and the mounting sleeves 24 are fixedly connected to the inner wall of the upper housing 18. Therefore, the battery units 26 are fixedly installed in the upper housing 18 through the mounting sleeves 24. Four connectors 25 are provided, and one connector 25 is distributed between two adjacent mounting sleeves 24. The two ends of the connectors 25 are respectively fixedly connected to two adjacent mounting sleeves 24 corresponding thereto. The mounting sleeves 24 and the connectors 25 enclose a passageway 27 through which the air flows through the drive module 5.

The air passing through the filter module 3 flows through the power supply module 4 through the passageway 27, so that the air can take away heat to the battery units 26 when the air flows, so that the power supply module 4 can better dissipate heat.

In order to improve the purification rate of the air by the air purifier, a negative ion generator module 42 is provided in the passageway 27. After the air is filtered by the activated carbon filter 21 and the HEPA filter 22, the particles such as smoke, germs, spores, and pollen in the air can be charged by the negative ions released by the negative ion generator module 42, and then they are further killed by the processing module 6 to achieve the double function of sterilization and purification. Negative ions can adhere to the dust, so that the dust stays in the air purifier for longer, thereby further improving the purification rate.

Referring to FIG. 2, the drive module 5 includes a fan unit. The fan unit provides a drive force to the air to drive the air to flow from the air inlets 1 to the air outlet 2.

Figure 8:
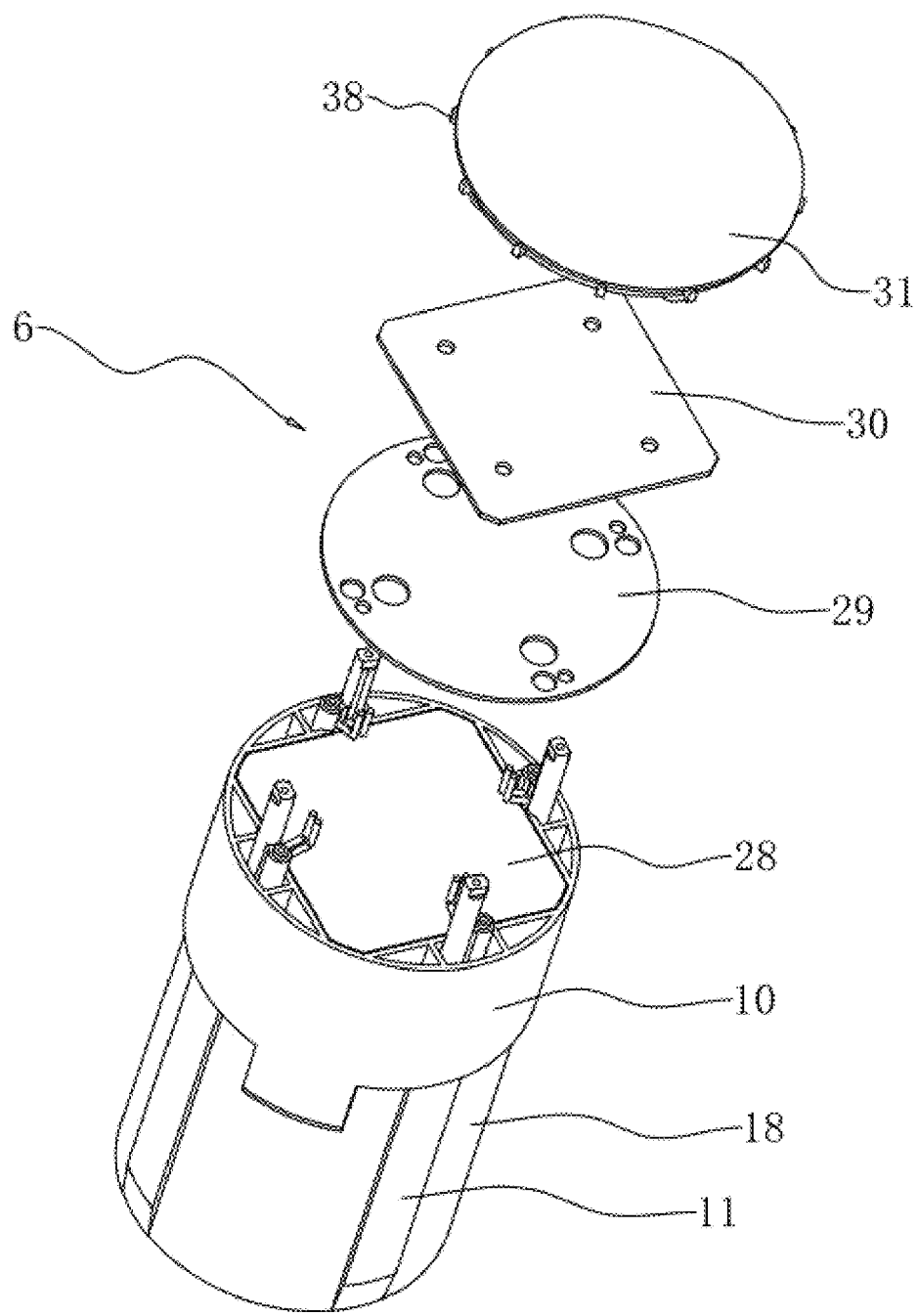
FIG. 8 is an exploded view of the embodiment with the outer housing and the filter module removed.

Referring to FIG. 8, the processing module 6 includes a titanium dioxide plate 28, an LED light plate 29, a circuit board 30 and a top cover 31 in turn from bottom to top. The top cover 31 is mounted on the upper end opening of the outer housing 8. The titanium dioxide plate 28 is inserted in the upper end of the upper housing 18. The top cover 31 is installed in the outer housing 8, and the circuit board 30 is fixedly installed on the inner side of the top cover 31. The LED light plate 29 is fixedly installed on the side of the circuit board 30 facing The titanium dioxide plate28. The LED light plate 29 irradiates UVA and UVC. The battery units 26 supply power to the LED light plate 29 and the circuit board 30 through wires.

When the air purifier is at work, the air after passing through the drive module 5 enters the processing module 6 for a secondary purification. The UVA and UVC irradiated by the LED light plate 29 destroy and change the DNA structure of microorganisms, so that the bacteria immediately die or cannot reproduce their offspring to achieve the purpose of sterilization. The titanium dioxide plate 28 will produce a photocatalytic reaction similar to photosynthesis under the irradiation of light, resulting in strong oxidative carboxyl free radicals and anionic free radicals, which can effectively decompose various organic compounds, destroy the cell membrane of bacteria and virus proteins, and remove organic pollutants. Therefore, the degree of air purification can be improved, so that the air is purified to the ideal state as much as possible.

Figure 9:
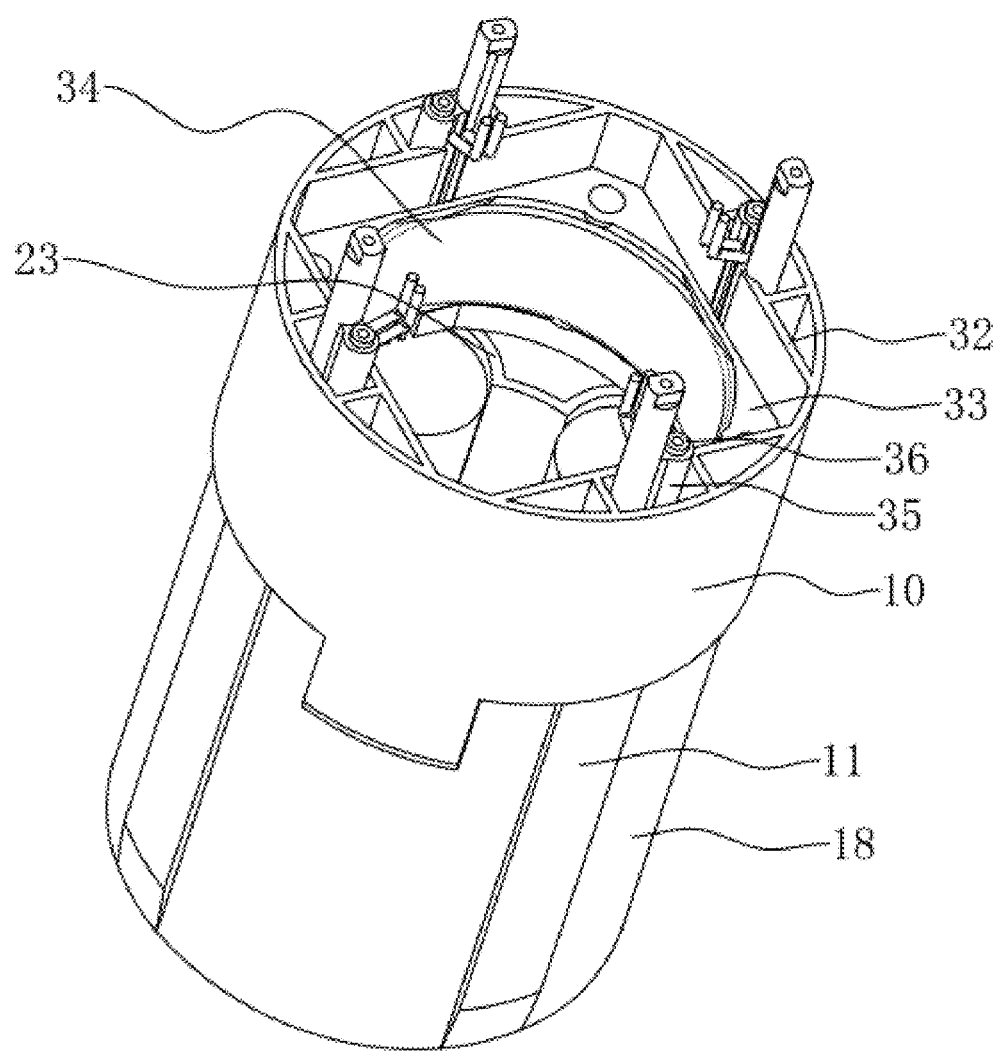
FIG. 9 is a schematic assembly view of an upper housing, a connection seat and a power supply module in the embodiment.

Specifically, referring to FIGS. 8 and 9, a connecting seat 32 is fixedly installed within the upper housing 18. The upper end face of the connecting seat 32 is provided with a first connecting groove 33 for insertion the titanium dioxide plate 28. The bottom surface of the first connecting groove 33 is provided with a second connecting groove 34 for insertion the fan unit, and the second connecting groove 34 communicates with the lower end face of the connecting seat 32. The fan unit is inserted in the second connecting groove 34 and abuts against the upper end face of the mounting seat 23 so that the fan unit is stably installed within the upper housing 18. The titanium dioxide plate 28 is inserted in the first connecting groove 33 and abuts against the inner wall of the first connecting groove 33, so that the titanium dioxide plate 28 is stably installed within the upper housing 18.

Figure 10:
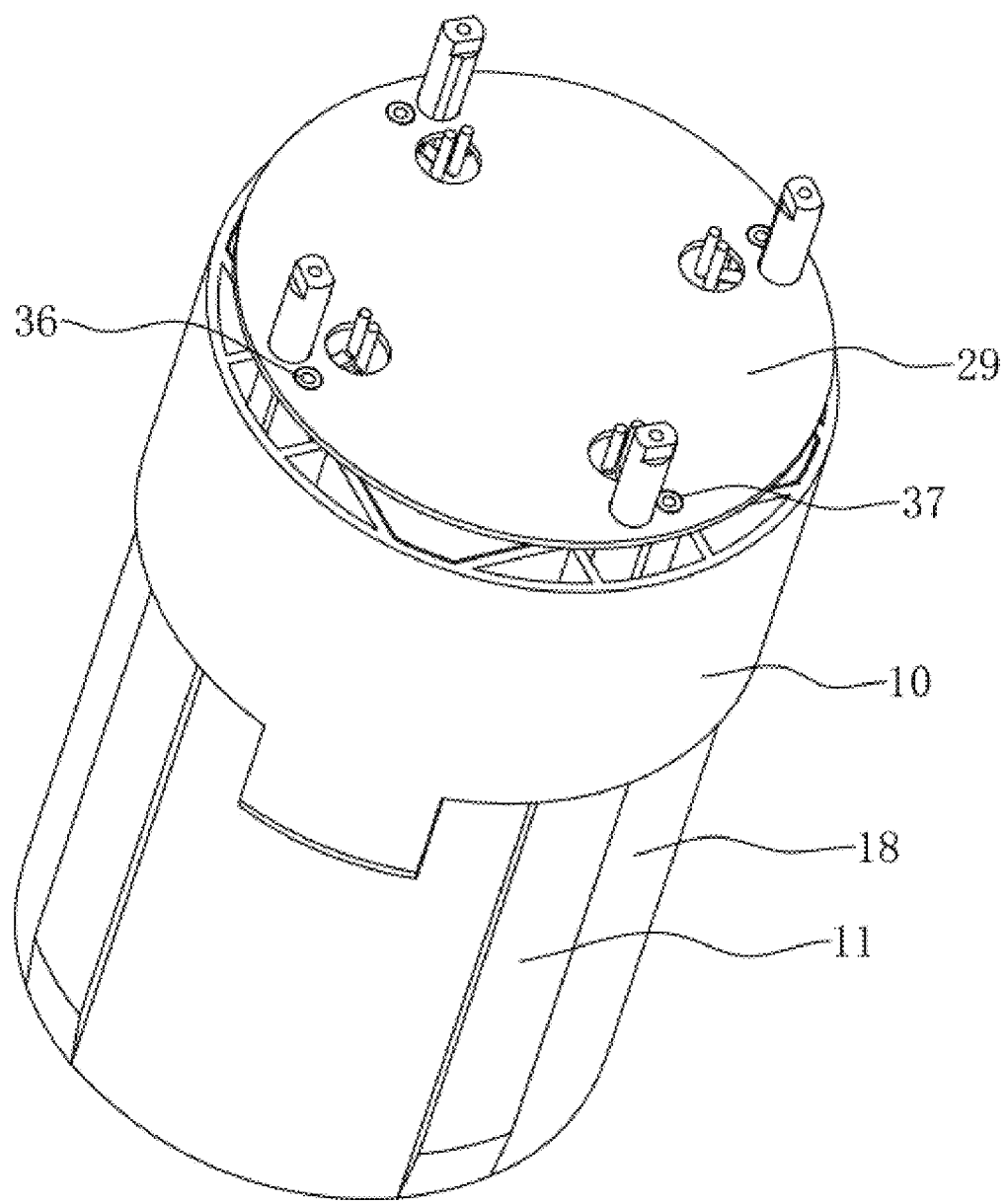
FIG. 10 is a schematic assembly view of the upper housing and an LED light plate in the embodiment.

Referring to FIGS. 9 and 10, the upper end of the inner housing 7 is fixedly installed with first mounting posts 35 along the axial direction thereof, and four first mounting posts 35 are provided along the circumferential direction of the upper housing 18. The upper end of the first mounting post 35 is fixedly mounted with a first mounting protrusion 36, and the LED light plate 29 is provided with first insertion grooves 37. The LED light plate 29 abuts against the first mounting posts 35 and the first mounting protrusions 36 are inserted in the first insertion grooves 37. Through the above structure, the LED light plate 29 is stably installed above the upper housing 18.

Figure 11:
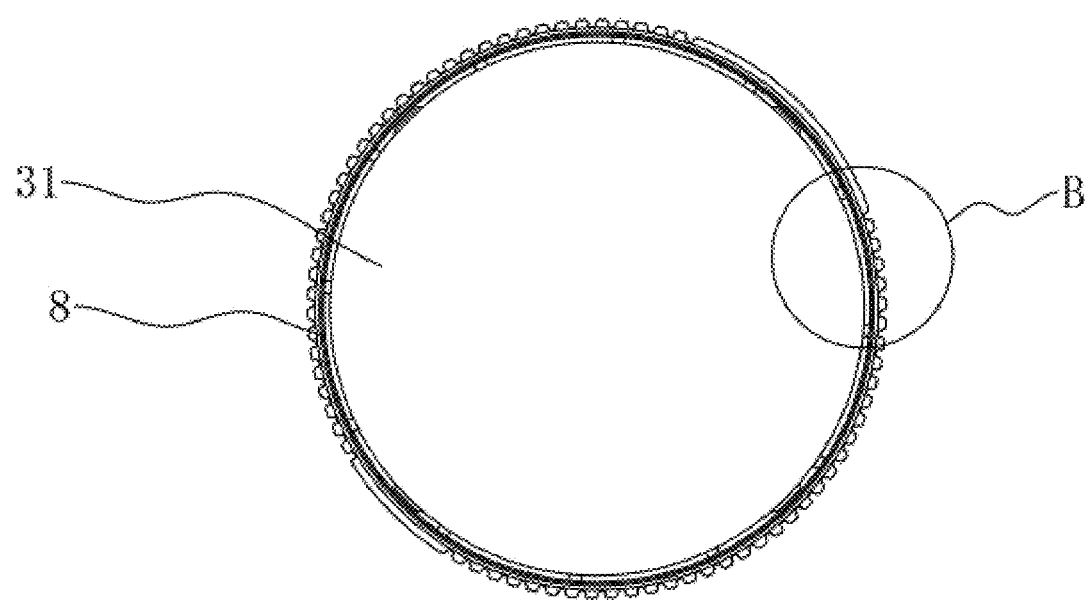
FIG. 11 is a top view of the embodiment.
Figure 12:
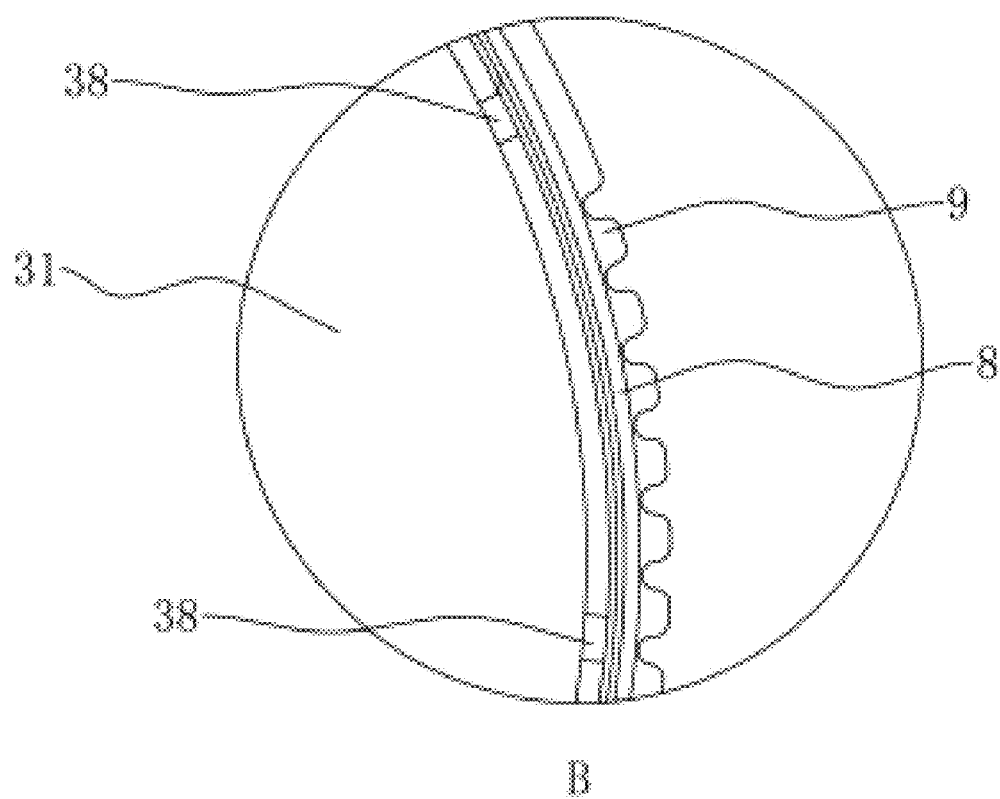
FIG. 12 is an enlarged view of part B in FIG. 11.

Referring to FIGS. 11 and 12, the outer wall of the top cover 31 is provided with mounting bumps 38, and a plurality of mounting bumps 38 are provided along the circumference of the top cover 31. When the top cover 31 is inserted in the upper end of the outer housing 8, the mounting bumps 38 abut against the outer wall of the outer housing 8 and form an interference fit with the outer housing 8. Thus, the top cover 31 is fixedly installed on the outer housing 8. The gap between the mounting bumps 38 can be used for the discharge of the air after the secondary purification.

Figure 13:
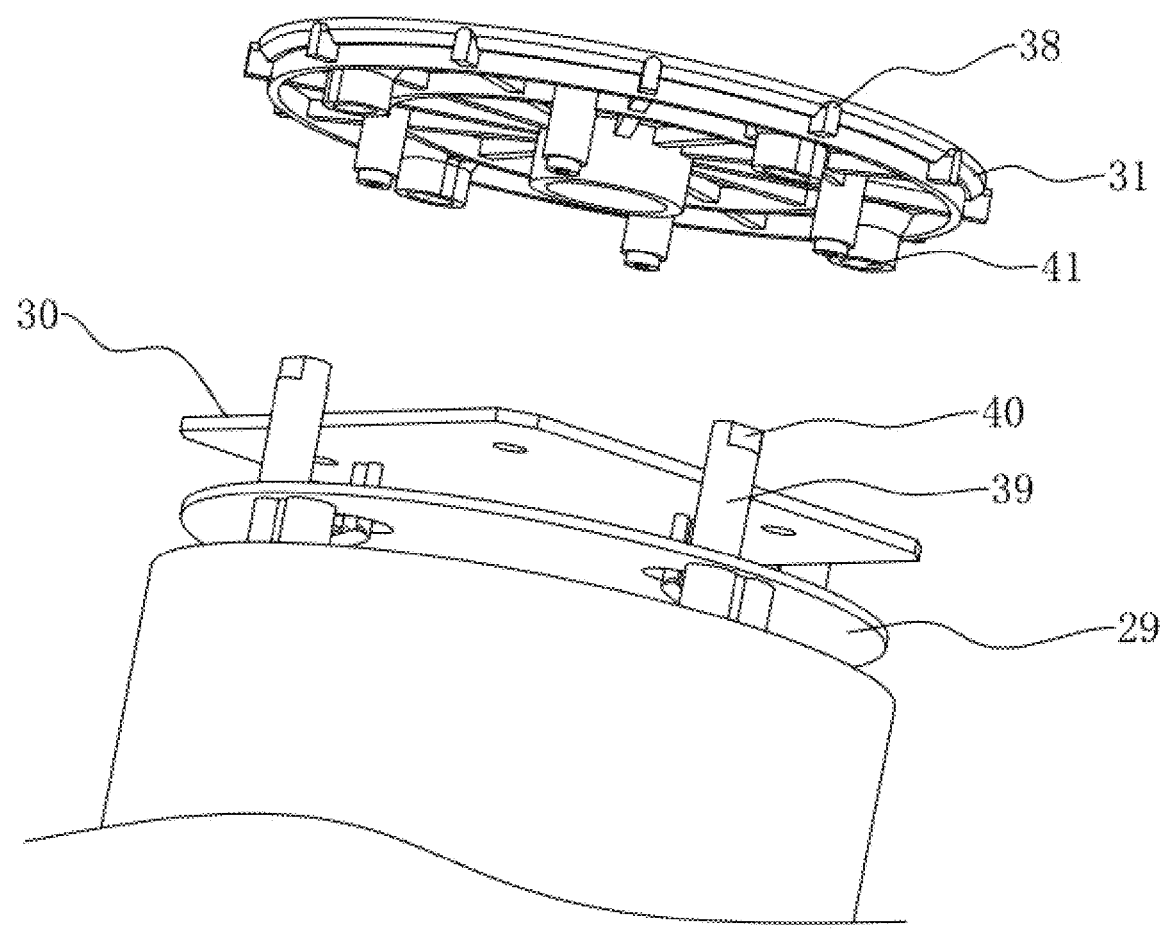
FIG. 13 is a schematic assembly view of the upper housing and a top cover in the embodiment.

Referring to FIG. 13, the upper end of the upper housing 18 is fixedly installed with second mounting posts 39 along its axial direction, and the second mounting posts 39 penetrate the LED light plate 29. Four second mounting posts 39 are provided along the circumferential direction of the upper housing 18. The distances between adjacent second mounting posts 39 are different. The upper end of the second mounting post 39 is fixedly mounted with a second mounting protrusion 40, and the top cover 31 is provided with second insertion grooves 41. The top cover 31 abuts against the second mounting posts 39 and the second mounting protrusions 40 are inserted in the second insertion grooves 41. The cooperation of the second mounting posts 39 and the second insertion grooves 41 can play a function of positioning, so that the top cover 31 is installed within the outer housing 8 according to a preset position. In addition, the friction force between the second mounting posts 39 and the second insertion grooves 41 can also enable the top cover 31 to be installed within the outer housing 8 more stably.

The implementation principle of the air purifier in the present invention embodiment is as follows.

1. When installing, the battery unit 26 is at first installed within the mounting sleeve 24;

2. The fan unit is installed within the first connecting slot 33, and The titanium dioxide plate 28 is installed within the second connecting slot 34;

3. The upper housing 18 installed with the battery unit 26, the fan unit and The titanium dioxide plate 28 is installed within the outer housing 8 from the upper end of the outer housing 8;

4. The filter module 3 is installed within the base 12, and then the base 12 is installed within the outer housing 8 from the lower end of the outer housing 8;

5. The LED light plate 29 is installed on the upper housing 18;

6. The top cover 31 with the circuit board 30 is installed to the upper end of the outer housing 8, thereby completing the installation;

7. The drive module 5 gives a drive force to the air, so that the air in turn flows through the air inlets 1, the diversion cavity 13, the air guide ports 14, the filter module 3, the power supply module 4, the drive module 5, the processing module 6 and the air outlet 2. A first purification (dust removal) is achieved as the air passes through the filter module 3, and a second purification (sterilization) is achieved as the air passes through the processing module 6, so as to realize the purification of the air.

The above are preferred embodiments of the present invention, and do not limit the scope of protection of the present invention accordingly. Therefore, all equivalent changes made in accordance with the structure, shape, and principle of the present invention shall be covered by the scope of protection of the present invention.

What is claimed is:

1. An air purifier, comprising a housing provided with an air inlet and an air outlet; wherein a filter module, a drive module and a processing module are sequentially arranged in the housing along an airflow direction; the drive module is used to drive the air to flow from the air inlet to the air outlet; the processing module in turn comprises a Titanium dioxide plate and an LED light plate sequentially installed in the housing along the airflow direction; and the LED light plate irradiates the Titanium dioxide plate, the LED light plate irradiating UVA and UVC, wherein the housing is provided upright; the housing comprises an inner housing and an outer housing sleeved outside the inner housing; a plurality of the air inlets are provided on an outer wall of the outer housing along the circumferential direction of the outer housing; the air outlet is provided on an upper end of the outer housing and communicated with an inner cavity of the inner housing; a lower end of the inner housing is provided with an air guide port communicated with the inner cavity of the inner housing; an outer wall of the inner housing is provided with convex edges along its length direction; the convex edges, the outer wall of the inner housing and an inner wall of the outer housing form a diversion cavity communicated with the air inlet and the air guide port; and the filter module, the drive module and the processing module are located between the air guide port and the air outlet.

2. The air purifier according to claim 1, wherein a plurality of air guide ribs are provided outside the outer housing along the axial direction of the outer housing and spaced apart along the circumferential direction of the outer housing; and the air inlets are located between the air guide ribs.

3. The air purifier according to claim 1, wherein the processing module further comprises a top cover installed with a circuit board; the LED light plate is connected with the circuit board; the upper end of the outer housing is provided in a form of an opening; and the top cover is installed at the upper end opening of the outer housing and is removably connected with the outer housing.

4. The air purifier according to claim 3, wherein an upper end of the inner housing is fixedly mounted along the axial direction thereof with at least two first mounting posts; an upper end of the first mounting post is fixedly mounted with a first mounting protrusion; the LED light plate is provided with first insertion grooves; and the LED light plate is abutted against the first mounting post and the first mounting protrusions are inserted into the first insertion grooves.

5. The air purifier according to claim 3, wherein an upper end of the inner housing is fixedly mounted along the axial direction thereof with at least two second mounting posts; an upper end of the second mounting post is fixedly mounted with a second mounting protrusion; the top cover is provided with a second insertion grooves; and the top cover is abutted against the second mounting post and the second mounting protrusions are inserted into the second insertion grooves.

6. The air purifier according to claim 1, wherein the inner housing comprises an upper housing and a lower housing located below the upper housing; the lower housing is removably connected with the outer housing; the filter module is installed within the lower housing; and the drive module is installed within the upper housing.

7. The air purifier according to claim 6, wherein a lower end of the outer housing is provided in a form of an opening, and the lower end opening of the outer housing is used to remove the lower housing.

8. The air purifier according to claim 7, wherein a lower end of the lower housing is fixedly provided with a base for closing the lower end of the lower housing and the lower end of the outer housing; and a plurality of the air guide ports are provided on a side wall of the lower housing along the circumferential direction of an outer wall of the lower housing.

9. The air purifier according to claim 8, wherein an upper end of the base is recessed downwards to form a plurality of overflow recesses provided along the radial direction of the base and along the circumferential direction of the lower housing, and one overflow recess corresponds to one air guide port.

10. The air purifier according to claim 1, wherein the filter module comprises an activated carbon filter and a HEPA filter that are sequentially disposed along the airflow direction.

11. The air purifier according to claim 1, wherein the drive module is removably connected with the inner housing.

12. The air purifier according to claim 1, wherein the power supply module is provided between the filter module and the drive module and is installed within the inner housing, and the air from the air inlet to the air outlet flows through the power supply module.

13. The air purifier according to claim 12, wherein the power supply module comprises a series of battery units that are disposed along the circumferential direction of the inner housing and a mounting seat that comprises a mounting sleeve sleeved outside the battery unit, one mounting sleeve corresponds to one battery unit, and the mounting sleeve is fixedly connected with the inner wall of the inner housing.

14. The air purifier according to claim 13, wherein the mounting seat further comprises a connector for fixedly connecting adjacent mounting sleeves; the mounting sleeve is circular in section; the mounting sleeve and the connector enclose a passageway through which the air flows through the drive module.

15. The air purifier according to claim 1, wherein a negative ion generator module is provided between the drive module and the filter module.

* * * * *